(12) United States Patent
Mitchell

(10) Patent No.: US 7,429,632 B2
(45) Date of Patent: Sep. 30, 2008

(54) METHOD OF MANUFACTURING SUPERABSORBENT POLYMERS

(75) Inventor: Michael A. Mitchell, Waxhaw, NC (US)

(73) Assignee: BASF Aktiengesellschaft, Ludwigshafen (DE)

( * ) Notice: Subject to any disclaimer, the term of this patent is extended or adjusted under 35 U.S.C. 154(b) by 218 days.

(21) Appl. No.: 10/591,365

(22) PCT Filed: Mar. 26, 2005

(86) PCT No.: PCT/EP2005/003209

§ 371 (c)(1),
(2), (4) Date: Sep. 1, 2006

(87) PCT Pub. No.: WO2005/095498

PCT Pub. Date: Oct. 13, 2005

(65) Prior Publication Data

US 2007/0203304 A1    Aug. 30, 2007

Related U.S. Application Data

(60) Provisional application No. 60/557,798, filed on Mar. 30, 2004.

(51) Int. Cl.
C08F 8/14    (2006.01)

(52) U.S. Cl. .............. 525/326.6; 525/328.5; 525/330.1; 525/384

(58) Field of Classification Search ............. 525/326.6, 525/328.5, 330.1, 384
See application file for complete search history.

(56) References Cited

U.S. PATENT DOCUMENTS

| | | | |
|---|---|---|---|
| 4,043,952 A | 8/1977 | Ganslaw et al. | |
| 4,051,086 A | 9/1977 | Reid | |
| 4,541,871 A | 9/1985 | Obayashi et al. | |
| 4,587,308 A | 5/1986 | Makita et al. | |
| 4,666,983 A | 5/1987 | Tsubakimoto et al. | |
| 4,734,478 A | 3/1988 | Tsubakimoto et al. | |
| 4,789,861 A | 12/1988 | Baggett et al. | |
| 4,824,901 A | 4/1989 | Alexander et al. | |
| 5,164,459 A | 11/1992 | Kimura et al. | |
| 5,385,983 A * | 1/1995 | Graham | 525/330.1 |
| 5,409,771 A | 4/1995 | Dahmen et al. | |
| 5,559,335 A | 9/1996 | Zeng et al. | |
| 5,669,894 A | 9/1997 | Goldman et al. | |
| 5,760,080 A * | 6/1998 | Wada et al. | 524/559 |
| 6,150,469 A * | 11/2000 | Harada et al. | 525/329.7 |
| 6,180,724 B1 * | 1/2001 | Wada et al. | 525/380 |
| 6,300,423 B1 * | 10/2001 | Engelhardt et al. | 525/381 |
| 6,639,022 B2 * | 10/2003 | Michels et al. | 525/329.1 |
| 6,720,389 B2 * | 4/2004 | Hatsuda et al. | 525/330.1 |
| 6,875,511 B2 * | 4/2005 | Dairoku et al. | 428/402 |
| 7,241,820 B2 * | 7/2007 | Smith et al. | 524/32 |
| 2002/0013394 A1 * | 1/2002 | Dairoku et al. | 524/109 |
| 2004/0176557 A1 | 9/2004 | Mertens et al. | |
| 2004/0180189 A1 | 9/2004 | Funk et al. | |
| 2006/0247377 A1 | 11/2006 | Riegel et al. | |

FOREIGN PATENT DOCUMENTS

| | | |
|---|---|---|
| DE | 40 20 780 | 8/1991 |
| EP | 0 509 708 | 10/1992 |
| WO | WO-92/16565 | 10/1992 |
| WO | WO-93/05080 | 3/1993 |
| WO | WO-99/42515 | 8/1999 |
| WO | WO-01/91815 | 12/2001 |
| WO | WO-02/20068 | 3/2002 |
| WO | WO-03/002623 | 1/2003 |
| WO | WO-2004/108795 | 12/2004 |

OTHER PUBLICATIONS

International Search Report in PCT/EP2005/003209 dated Jun. 16, 2005.

* cited by examiner

*Primary Examiner*—Bernard Lipman
(74) *Attorney, Agent, or Firm*—Marshall, Gerstein & Borun LLP

(57) ABSTRACT

An improved method of manufacturing surface-crosslinked superabsorbent polymer particles is disclosed. The superabsorbent polymer particles are surface crosslinked using about 20 to about 35 wt % of 1,3-propanediol as a cosolvent in a surface-crosslinking step. The use of 1,3-propanediol as a cosolvent reduces the amount of surface-crosslinking agent required to adequately surface crosslink the superabsorbent polymer, and reduces or eliminates the fouling of process equipment attributed to previous cosolvents used in a surface crosslinking step.

12 Claims, 1 Drawing Sheet

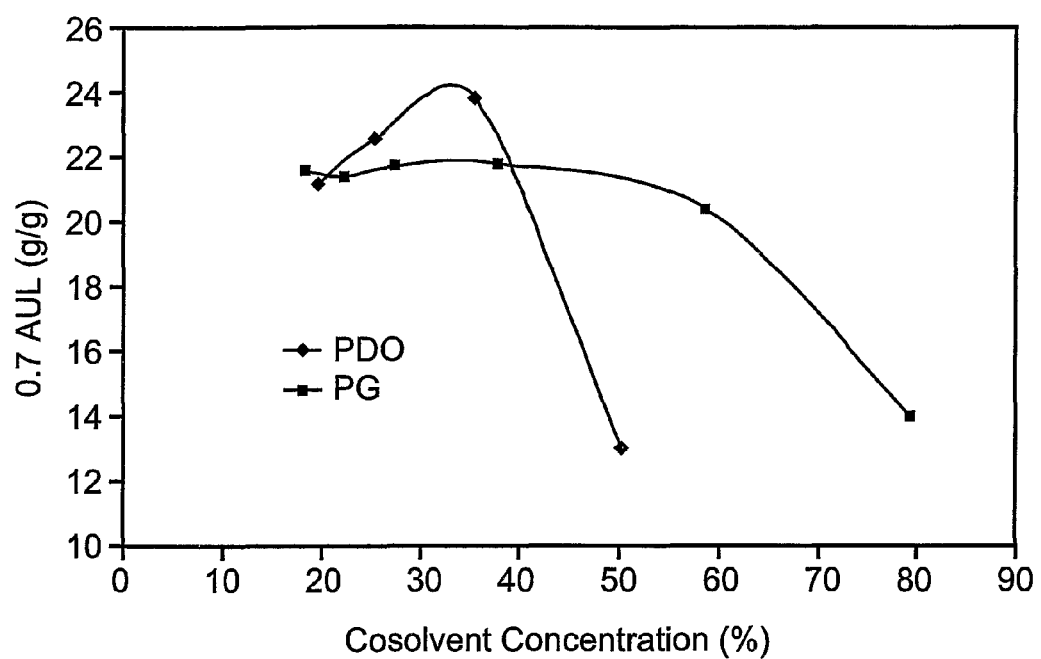

METHOD OF MANUFACTURING SUPERABSORBENT POLYMERS

CROSS-REFERENCE TO RELATED APPLICATIONS

This is the U.S. national phase application of International Application No. PCT/EP2005/003209, filed Mar. 26, 2005, which claims the benefit of provisional U.S. patent application No. 60/557,798, filed Mar. 30, 2004.

FIELD OF THE INVENTION

The present invention relates to surface-crosslinked superabsorbent polymer particles, and to an improved method of producing the surface-cross-linked superabsorbent particles. More particularly, the present invention relates to the use of 1,3-propanediol (PDO) as a cosolvent during a surface-crosslinking step in the manufacture of an SAP.

BACKGROUND OF THE INVENTION

Water-absorbing resins are widely used in sanitary goods, hygienic goods, wiping cloths, water-retaining agents, dehydrating agents, sludge coagulants, disposable towels and bath mats, disposable door mats, thickening agents, disposable litter mats for pets, condensation-preventing agents, and release control agents for various chemicals. Water-absorbing resins are available in a variety of chemical forms, including substituted and unsubstituted natural and synthetic polymers, such as hydrolysis products of starch acrylonitrile graft polymers, carboxymethylcellulose, crosslinked polyacrylates, sulfonated polystyrenes, hydrolyzed polyacrylamides, polyvinyl alcohols, polyethylene oxides, polyvinylpyrrolidones, and polyacrylonitriles.

Such water-absorbing resins are termed "superabsorbent polymers," or SAPs, and typically are lightly crosslinked hydrophilic polymers. SAPs are generally discussed in Goldman et al. U.S. Pat. Nos. 5,669,894 and 5,559,335, the disclosures of which are incorporated herein by reference. SAPs can differ in their chemical identity, but all SAPs are capable of absorbing and retaining amounts of aqueous fluids equivalent to many times their own weight, even under moderate pressure. For example, SAPs can absorb one hundred times their own weight, or more, of distilled water. The ability to absorb aqueous fluids under a confining pressure is an important requirements for an SAP used in a hygienic article, such as a diaper.

As used herein, the term "SAP particles" refers to superabsorbent polymer particles in the dry state, i.e., particles containing from no water up to an amount of water less than the weight of the particles. The term "particles" refers to granules, fibers, flakes, spheres, powders, platelets, and other shapes and forms known to persons skilled in the art of superabsorbent polymers. The terms "SAP gel" and "SAP hydrogel" refer to a superabsorbent polymer in the hydrated state, i.e., particles that have absorbed at least their weight in water, and typically several times their weight in water. The term "surface crosslinking" means that the level of functional crosslinks in the SAP particle in the vicinity of the surface of the particle is generally higher than the level of functional crosslinks in the SAP particle in the interior of the particle. The term "surface-crosslinked SAP particle" refers to an SAP particle having its molecular chains present in the vicinity of the particle surface cross-linked by a compound applied to the surface of the particle.

Initially, the swelling capacity of an SAP particle on contact with liquids, also referred to as free swelling capacity, was the main factor in the design and development of SAP particles. Later, however, it was found that not only is the amount of absorbed liquid important, but the stability of the swollen gel, or gel strength, also is important. The free swelling capacity, on one hand, and the gel strength, on the other hand, represent contrary properties. Accordingly, SAP particles having a particularly high absorbency typically exhibit a poor gel strength, such that the gel deforms under pressure (e.g., the load of a body), and prevents further liquid distribution and absorption.

A balanced relation between absorptivity (gel volume) and gel strength is desired to provide proper liquid absorption, liquid transport, and dryness of a diaper and the skin when using SAP particles in a diaper. In this regard, not only is the ability of SAP particles to retain a liquid under subsequent pressure an important property, but absorption of a liquid against a simultaneously acting pressure, i.e., during liquid absorption also is important. This is the case in practice when a child or adult sits or lies on a sanitary article, or when shear forces are acting on the sanitary article, e.g., leg movements. This absorption property is referred to as absorption under load.

Investigators have researched various methods of improving the amount of liquid absorbed and retained by SAP particles, especially under load, and the rate at which the liquid is absorbed. One preferred method of improving the absorption and retention properties of SAP particles is to surface crosslink the SAP particles.

As understood in the art, surface-crosslinked SAP particles have a higher level of crosslinking in the vicinity of the surface than in the interior. As used herein, "surface" describes the outer-facing boundaries of the particle. For porous SAP particles, exposed internal surface also are included in the definition of surface.

Surface-crosslinked SAP particles under pressure, in general, exhibit higher liquid absorption and retention values than SAP particles having a comparable level of internal crosslinks, but lacking surface crosslinking. Internal crosslinks arise from polymerization of monomers comprising the SAP particles, and are present in the polymer backbone. It has been theorized that surface crosslinking increases the resistance of SAP particles to deformation, thus reducing the degree of contact between surfaces of neighboring SAP particles when the resulting hydrogel is deformed under an external pressure. The degree to which absorption and retention values are enhanced by surface crosslinking is related to the relative amount and distribution of internal and surface crosslinks, and to the particular surface-crosslinking agent and method of surface crosslinking.

The surface crosslinking of SAP particles using crosslinking agents having two or more functional groups capable of reacting with pendant carboxylate or other groups contained on the polymer comprising the SAP particle is disclosed in various patents. For example, U.S. Pat. No. 4,043,952 discloses the use of polyvalent metal compounds as surface-crosslinking compounds. U.S. Pat. No. 4,051,086 discloses the use of glyoxal as a surface crosslinker to improve the absorption rate of SAP particles.

Surface-crosslinking agents include, but are not limited to, diglycidyl ethers, halo epoxy compounds, polyols, polyamines, polyisocyanates, polyfunctional aziridine compounds, and di- or tri-alkylhalides. Regardless of the identity of the surface-cross-linking agent, the agent used for the surface crosslinking has at least two functional groups, and the SAP particles are heated after the surface-crosslinking agent is applied to the surface of the SAP particles.

Prior methods of performing surface cross-linking of SAP particles are disclosed, for example, in U.S. Pat. No. 4,541,871, WO 92/16565, WO 93/05080, U.S. Pat. Nos. 4,824,901; 4,789,861; 4,587,308; 4,734,478; 5,164,459; 4,666,983; 5,385,983; DE 40 20 780, and EP 0 509,708. Surface crosslinking of SAPs is generally discussed in F. L. Buchholz et al., ed., "Modern Superabsorbent Polymer Technology," Wiley-VCH, New York, N.Y., pages 97-108 (1998).

As disclosed in the art, the SAP particles are either mixed with the surface-crosslinking agent optionally using small amounts of water and/or an organic solvent, or an SAP hydrogel containing 10% to 40%, by weight, water is dispersed in a hydrophilic or hydrophobic solvent and mixed with the surface-crosslinking agent.

One problem encountered in prior methods of surface crosslinking SAP particles is the use of propylene glycol as a cosolvent for the surface-crosslinking agent. Propylene glycol has a relatively high vapor pressure, and is oxidized relatively easily, which adversely affect both the surface-crosslinking method and process equipment, and results in surface-crosslinked SAPs having inconsistent properties. Using propylene glycol as a cosolvent results in the fouling of process equipment attributed to the formation of oxidation and recombination by-products. Propylene glycol volatility also leads to inconsistent and decreased SAP performance.

The present invention is directed to methods of surface-crosslinking SAP particles that overcome the disadvantages associated with prior surface-crosslinking methods which utilize propylene glycol as a cosolvent.

SUMMARY OF THE INVENTION

The present invention is directed to a method of surface-crosslinking SAP particles using 1,3-propanediol (PDO) as a cosolvent in an aqueous solution of a surface-crosslinking agent. In particular, the present invention is directed to a method wherein a surface-crosslinker solution containing water, a surface-crosslinking agent, and about 20 to about 35 wt % PDO is used to surface treat SAP particles. After application of the surface-crosslinker solution to the SAP particles, the resulting particles are heated at about 25° C. to about 150° C. for about 15 to about 180 minutes to allow the surface-crosslinking agent to form cross-links on the SAP particle surfaces. The present method is especially useful in the surface cross-linking of polyacrylate salts, hydrolyzed polyacrylamides, and SAPs having a plurality of pendant neutralized carboxyl groups.

In accordance with the present invention, the method allows the amount of surface-crosslinking agent in the surface-crosslinker solution to be reduced, while providing equivalent surface crosslinking provided by a composition containing propylene glycol, i.e., 1,2-propanediol, and a greater amount of surface-crosslinking agent. The amount of surface-crosslinking agent in the surface-crosslinker solution can be decreased by at least 5 wt %, and typically 10 to 25 wt %, when PDO is used as a cosolvent.

By replacing PG with 1,3-propanediol, which has a lower volatility and greater oxidative stability compared to propylene glycol, better SAP performance was achieved while maintaining low residual amounts of surface-crosslinking agent on the SAP particles. The use of PDO also has allowed for lower use levels of the surface crosslinking agent and lower cosolvent levels, i.e., less PDO is required compared to PG in the surface-crosslinking process. In particular, PG is used as a cosolvent in amounts of about 35 to about 50 wt %.

In contrast, PDO is used as a cosolvent in an amount of about 20 to about 35 wt %, and preferably about 25 to about 30 wt %.

Therefore, one aspect of the present invention is to provide a method of manufacturing surface-crosslinked SAP particles comprising applying a sufficient amount of a surface-crosslinker solution to surfaces of the SAP particles to provide surface-treated SAP particles, said surface-crosslinker solution comprising a surface-crosslinking agent, water, and about 20 to about 35 wt % of PDO as a cosolvent; then heating the surface-treated SAP particles at a sufficient temperature for a sufficient time for the surface-crosslinking agent to react with pendant groups on a polymer comprising the SAP particle to form surface crosslinks on the SAP particle.

Another aspect of the present invention is to heat the surface-treated SAP particles at about 25° C. to about 150° C. for about 15 to about 180 minutes to form surface crosslinks on the SAP particles, wherein the PDO forms essentially no surface crosslinks on the SAP particle.

Another aspect of the present invention is to provide surface-crosslinked particles having improved performance compared to particles surface crosslinked in the presence of PG, and to overcome problems associated with prior cosolvents used in a surface-crosslinking step, for example, propylene glycol.

Another aspect of the present invention is to provide a method of manufacturing surface-cross-linked SAP particles utilizing PDO as a cosolvent in the surface-crosslinker solution to substantially reduce equipment malfunction and to reduce operation costs.

These and other aspects and advantages of the present invention will become apparent from the following detailed description of the preferred embodiments.

BRIEF DESCRIPTION OF THE DRAWING

FIG. 1 contains plots of AUL (0.7 psi, g/g) vs. cosolvent concentration showing the effects of PDO and PG on AUL (0.7).

DETAILED DESCRIPTION OF THE PREFERRED EMBODIMENTS

In accordance with the present invention, SAP particles are surface crosslinked to substantially increase the amount and rate of liquid absorption, and the overall retention of liquids, by the SAP particles. Surface crosslinking of the SAP particles at any time after polymerization and sufficient drying to form solid SAP particles improves SAP absorption properties. For economics and ease of manufacture, surface crosslinking is most advantageously performed immediately after the SAP particles are synthesized, dried to an appropriate water content, and sized, such as by grinding.

As will become apparent from the following detailed description of the preferred embodiments, treating an SAP with a surface-crosslinker solution containing PDO as a cosolvent for the surface-crosslinking agent facilitates the surface-crosslinking step; overcomes problems associated with prior cosolvents, and especially propylene glycol; reduces fouling of process equipment; reduces costs; and provides surface-crosslinked SAPs having improved performance and more consistent performance.

As stated above, surface crosslinking of SAP particles is well known. However, many surface-crosslinking methods exhibit disadvantages. Some disadvantages can be attributed to the surface-crosslinking agent. However, other disadvantages can be attributed to the organic cosolvents typically used in the aqueous surface-crosslinker solution.

The cosolvent typically is a low molecular weight organic compound, such as an alcohol, diol, or ketone. The alcohol and ketone cosolvents have the problems of high volatility, flammability, and the need for solvent recovery. Propylene glycol (PG) is widely used as a cosolvent, but has the problems of a relatively high vapor pressure, a tendency to oxidize, and an unpleasant odor when residual PG is released from wetted SAP particles.

The propylene glycol oxidation and vaporization products foul process equipment, which then must be cleaned. In addition, fouled process equipment can contaminate the SAP particles requiring the particles to be discarded or reworked to provide a consumer acceptable product.

The present invention is directed to the use of PDO as a cosolvent in a surface-crosslinker solution. PDO has been used in surface-crosslinking processes previously. U.S. Patent Application Publication No. 2002/0002226 discloses the use of PDO as a surface-crosslinking agent, and specifically states that the PDO is not to be considered as a solvent. U.S. Pat. No. 6,562,879 also discloses that PDO can be used as a surface-crosslinking agent. WO 03/031482 generally discloses alcohols, including PDO, as a cosolvent in a surface-crosslinking step. A disadvantage of PDO, and other diols and polyols used as surface-crosslinking agents, is the high temperature required to effect surface crosslinking and long reaction times.

The identity of the SAP particles surface crosslinked in the present invention is not limited. The SAP particles are prepared by methods well known in the art, for example, solution or emulsion polymerization. The SAP particles can comprise an acidic water-absorbing resin, a basic water-absorbing resin, a blend of an acidic and basic water-absorbing resin, or a multicomponent SAP particle as disclosed in U.S. Pat. No. 6,072,101, the disclosure of which is incorporated herein by reference. Of particular utility are SAP particles containing a plurality of pendant, neutralized carboxyl groups along the polymer chain.

The SAP particles can be prepared, for example, by:

(1) copolymerizing an acrylate salt and a crosslinking monomer in aqueous solution, and drying the resulting gel-like hydrous polymer by heating;

(2) dispersing an aqueous solution of acrylic acid and/or an alkali metal acrylate, a water-soluble radical polymerization initiator, and a crosslinkable monomer in an alicyclic and/or an aliphatic hydrocarbon solvent in the presence of a surface active agent, and subjecting the mixture to suspension polymerization;

(3) saponifying copolymers of vinyl esters and ethylenically unsaturated carboxylic acids or their derivatives;

(4) polymerizing starch and/or cellulose, a monomer having a carboxyl group or capable of forming a carboxyl group upon hydrolysis, and a crosslinking monomer in an aqueous medium, and, as required, hydrolyzing the resulting polymer; or (5) reacting an alkaline substance with a maleic anhydride-type copolymer containing maleic anhydride and at least one monomer selected from α-olefins and vinyl compounds, and, as required, reacting the reaction product with a polyepoxy compound.

Other methods and monomers that provide SAP particles also are known in the art.

Generally, acidic water-absorbing resins have carboxylate, sulfonate, sulfate, and/or phosphate groups incorporated along the polymer chain. Polymers containing these acid moieties are synthesized either from monomers previously substituted with one or more of these acidic functional groups or by incorporating the acidic functional group into the polymer after synthesis. To incorporate carboxyl groups into a polymer, any of a number of ethylenically unsaturated carboxylic acids can be homopolymerized or copolymerized. Carboxyl groups also can be incorporated into the polymer chain indirectly by hydrolyzing a homopolymer or copolymer of monomers such as acrylamide, acrylonitrile, methacrylamide, and alkyl acrylates or methacrylates.

An acidic water-absorbing resin present in an SAP particle can be either a strong or a weak acidic water-absorbing resin. The acidic water-absorbing resin can be a single resin, or a mixture of resins. The acidic resin can be a homopolymer or a copolymer.

The acidic water-absorbing resin typically is a neutralized, lightly crosslinked acrylic-type resin, such as neutralized, lightly cross-linked polyacrylic acid. The lightly crosslinked acidic resin typically is prepared by polymerizing an acidic monomer containing an acyl moiety, e.g., acrylic acid, or a moiety capable of providing an acid group, i.e., acrylonitrile, in the presence of a free radical crosslinker, i.e., a polyfunctional organic compound. The acidic resin can contain other copolymerizable units, i.e., other monoethylenically unsaturated comonomers, well known in the art, as long as the polymer is substantially, i.e., at least 10%, and preferably at least 25%, acidic monomer units. To achieve the full advantage of the present invention, the acidic resin contains at least 50%, and more preferably, at least 75%, and up to 100%, acidic monomer units. The acidic resin is neutralized at least 50 mole %, and preferably at least 70 mole %, with a base prior to surface crosslinking.

Ethylenically unsaturated carboxylic acid and carboxylic acid anhydride monomers, and salts, useful in the acidic water-absorbing resin include acrylic acid, methacrylic acid, ethacrylic acid, α-chloroacrylic acid, α-cyanoacrylic acid, 1-methylacrylic acid (crotonic acid), α-phenylacrylic acid, β-acryloxypropionic acid, sorbic acid, α-chlorosorbic acid, angelic acid, cinnamic acid, p-chlorocinnamic acid, β-stearylacrylic acid, itaconic acid, citraconic acid, mesaconic acid, glutaconic acid, aconitic acid, maleic acid, fumaric acid, tricarboxyethylene, 2-methyl-2-butene dicarboxylic acid, maleamic acid, N-phenyl maleamide, maleamide, maleic anhydride, fumaric anhydride, itaconic anhydride, citraconic anhydride, mesaconic anhydride, methyl itaconic anhydride, ethyl maleic anhydride, diethylmaleate, methylmaleate, and maleic anhydride.

Sulfonate-containing acidic resins can be prepared from monomers containing functional groups hydrolyzable to the sulfonic acid form, for example, alkenyl sulfonic acid compounds and sulfoalkylacrylate compounds. Ethylenically unsaturated sulfonic acid monomers include aliphatic or aromatic vinyl sulfonic acids, such as vinyl sulfonic acid, allyl sulfonic acid, vinyl toluene sulfonic acid, styrene sulfonic acid, acrylic and methacrylic sulfonic acids, such as sulfoethyl acrylate, sulfoethyl methacrylate, sulfopropyl acrylate, 2-vinyl-4-ethylbenzene, 2-allylbenzene sulfonic acid, 1-phenylethylene sulfonic acid, sulfopropyl methacrylate, 2-hydroxy-3-methacryloxypropyl sulfonic acid, and 2-acrylamide-2-methylpropane sulfonic acid.

Sulfate-containing acidic resins are prepared by reacting homopolymers or copolymers containing hydroxyl groups or residual ethylenic unsaturation with sulfuric acid or sulfur trioxide. Examples of such treated polymers include sulfated polyvinylalcohol, sulfated hydroxyethyl acrylate, and sulfated hydroxypropyl methacrylate. Phosphate-containing acidic resins are prepared by homopolymerizing or copolymerizing ethylenically unsaturated monomers containing a phosphoric acid moiety, such as methacryloxy ethyl phosphate.

Copolymerizable monomers for introduction into the acidic resin, or into the basic resin, include, but are not limited to, ethylene, propylene, isobutylene, $C_{1-4}$ alkyl acrylates and methacrylates, vinyl acetate, methyl vinyl ether, and styrenic compounds having the formula:

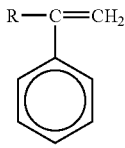

wherein R represents hydrogen or a $C_{1-6}$ alkyl group, and wherein the phenyl ring optionally is substituted with one to four $C_{1-4}$ alkyl or hydroxy groups.

Suitable $C_{1-4}$ alkyl acrylates include, but are not limited to, methyl acrylate, ethyl acrylate, isopropyl acrylate, n-propyl acrylate, n-butyl acrylate, and the like, and mixtures thereof. Suitable $C_{1-6}$ alkyl methacrylates include, but are not limited to, methyl methacrylate, ethyl methacrylate, isopropyl methacrylate, n-propylmethylmethacrylate, n-butyl methacrylate, and the like, and mixtures thereof or with $C_{1-4}$ alkyl acrylates. Suitable styrenic compounds include, but are not limited to, styrene, α-methylstyrene, p-methylstyrene, t-butyl styrene, and the like, and mixtures thereof or with $C_{1-4}$ alkyl acrylates and/or methacrylates.

The polymerization of acidic monomers, and optional copolymerizable monomers, most commonly is performed by free radical processes in the presence of a polyfunctional organic compound. The acidic resins are internally crosslinked to a sufficient extent such that the polymer is water insoluble. Internal crosslinking renders the acidic resins substantially water insoluble, and, in part, serves to determine the absorption capacity of the resins. For use in absorption applications, an acidic resin is lightly crosslinked, i.e., has an internal cross-linking density of less than about 20%, preferably less than about 10%, and most preferably about 0.01% to about 7%.

An internal crosslinking agent most preferably is used in an amount of less than about 7 wt %, and typically about 0.1 wt % to about 5 wt %, based on the total weight of monomers. Examples of internal crosslinking polyvinyl monomers include, but are not limited to, polyacrylic (or polymethacrylic) acid esters represented by the following formula (I); and bisacrylamides, represented by the following formula (II).

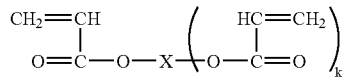

wherein X is ethylene, propylene, trimethylene, cyclohexyl, hexamethylene, 2-hydroxypropylene, —($CH_2CH_2O$)$_p$$CH_2CH_2$—, or

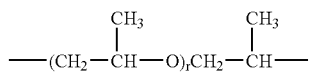

p and r are each an integer 5 to 40, and k is 1 or 2;

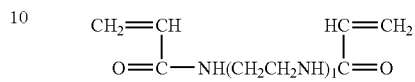

wherein 1 is 2 or 3.

Specific internal crosslinking monomers include, but are not limited to, 1,4-butanediol diacrylate, 1,4-butanediol dimethacrylate, 1,3-butylene glycol diacrylate, 1,3-butylene glycol dimethacrylate, diethylene glycol diacrylate, diethylene glycol dimethacrylate, ethoxylated bisphenol A diacrylate, ethoxylated bisphenol A dimethacrylate, ethylene glycol dimethacrylate, 1,6-hexanediol diacrylate, 1,6-hexanediol dimethacrylate, neopentyl glycol dimethacrylate, polyethylene glycol diacrylate, polyethylene glycol dimethacrylate, triethylene glycol diacrylate, triethylene glycol dimethacrylate, tripropylene glycol diacrylate, tetraethylene glycol diacrylate, tetraethylene glycol dimethacrylate, dipentaerythritol pentaacrylate, pentaerythritol tetraacrylate, pentaerythritol triacrylate, trimethylolpropane triacrylate, trimethylolpropane trimethacrylate, tris(2-hydroxyethyl)isocyanurate triacrylate, tris(2-hydroxyethy)isocyanurate trimethacrylate, divinyl esters of a polycarboxylic acid, diallyl esters or a polycarboxylic acid, triallyl terephthalate, diallyl maleate, diallyl fumarate, hexamethylenebismaleimide, trivinyl trimellitate, divinyl adipate, diallyl succinate, a divinyl ether of ethylene glycol, cyclopentadiene diacrylate, tetraallyl ammonium halides, trimethylolpropane triacrylate, or mixtures thereof. Compounds such as divinylbenzene and divinyl ether also can be used to internally crosslink the polymers. Especially preferred crosslinking agents are N,N'-methylenebisacrylamide, N,N'-methylenebismethacrylamide, ethylene glycol dimethacrylate, and trimethylolpropane triacrylate.

One or more initiator is added to the aqueous solution of the monomers and internal cross-linking agent to facilitate polymerization. Often the initiator comprises at least one thermal initiator and at least one redox initiator. Nonlimiting examples of useful redox initiators include a reducing agent, such as a sulfite or bisulfite of an alkali metal, such as ammonium sulfite, ammonium bisulfite, or ammonium metabisulfite, a persulfate of an alkali metal or ammonium persulfate, t-butyl butyl hydroperoxide, di-t-butyl hydroperoxice, t-butyl perbenzoate, t-butyl peroxy isopropyl carbonate, and peroxy-3,3,5-trimethylcyclohexane. These redox initiators can be used singly or in a suitable combination. Of these, especially preferred are a redox initiator including a combination of ammonium persulfate and sodium hydrogen sulfite. The redox initiator is used in an amount, calculated as solids, of about 0.1% to about 10%, preferably about 0.5% to about 5%, of the combined weight of the monomers and internal crosslinking agent. Depending on the amount and kind of the initiator, the initiator is used with isopropyl alcohol, an alkyl mercaptan, or other chain transfer agent to control the molecular weight of the polymer obtained.

Examples of suitable thermal initiators include, but are not limited to, azo initiators such as azobisisobutyronitrile, 4-t- butylazo-4'-cyanovaleric acid, 4,4'-azobis(4-cyanovaleric acid), 2,2'-azobis(2-amidinopropane)dihydrochloride, 2,2'-azobis(2,4-dimethylvaleronitrile), dimethyl 2,2'-azobisisobutyrate, 2,2'-azobis(2,4-dimethylvaleronitrile), (1-phenylethyl)azodiphenyl methane, 2,2'-azobis(2-methylbutyronitrile), 1,1'-azobis(1-cyclohexanecarbonitrile), 2-(carbamoylazo)isobutyronitrile, 2,2'-azobis(2,4,4-trimethylpentane), 2-phenylazo-2,4-dimethyl-4-methoxyvaleronitrile, 2,2'-azobis(2-methylpropane), 2,2'-azobis(N,N'-dimethyleneisobutyramidine)dihydrochloride), 2,2'-azobis(N,N'-dimethyleneisobutyramidine), 4,4'-azobis(4-cyanopentanoic acid), 2,2-azobis(2-methyl-N-[1,1-bis(hydroxymethyl)-2-hydroxy-ethyl]propionamide), 2,2'-azobis[2-methyl-N-[1,1-bis(hydroxymethyl)ethyl] propionamide), 2,2-azobis(2-methyl-N-(2-hydroxyethyl) propionamide], 2,2'-azobis(isobutyramide)dihydrate, and mixtures thereof.

Ultraviolet (UV) light also can be used to effect polymerization of the monomers. UV light can be used in conjunction with a redox initiator and/or a free radical initiator. When UV light is utilized in the polymerization step, a photoinitiator also is added to the reaction mixture. The photoinitiator is used in a standard amount well known to persons skilled in the art. Suitable photoinitiators include, but are not limited to, 2-hydroxy-1-[4-hydroxyethoxy)phenyl]-2-methyl-1-propanone, which is commercially available from Ciba Additives of Hawthorne, N.Y., as IRGACURE 2959, and 2-hydroxy-2-methyl-1-phenyl-1-propanone, which also is commercially available from Ciba Additives as DAROCUR 1173.

The acidic resin, either strongly acidic or weakly acidic, can be any resin that acts as an SAP in its neutralized form. Examples of acidic resins include, but are not limited to, polyacrylic acid, hydrolyzed starch-acrylonitrile graft copolymers, starch-acrylic acid graft copolymers, saponified vinyl acetate-acrylic ester copolymers, hydrolyzed acrylonitrile copolymers, hydrolyzed acrylamide copolymers, ethylene-maleic anhydride copolymers, isobutylene-maleic anhydride copolymers, poly(vinylsulfonic acid), poly(vinylphosphonic acid), poly(vinylphosphoric acid), poly(vinylsulfuric acid), sulfonated polystyrene, poly(aspartic acid), poly(lactic acid), and mixtures thereof. The preferred acidic resins are the polyacrylic acids.

The SAP particle contains about 50 to 100 percent neutralized pendant carboxylate salt units. Accordingly, it may be necessary to neutralize carboxylic acid groups. Neutralization of carboxylic acid groups is accomplished using a strong organic or inorganic base, such as sodium hydroxide, potassium hydroxide, ammonia, ammonium hydroxide, or an organic amine, by methods well known in the art.

Analogous to the acidic resin, a basic water-absorbing resin present in the SAP particles can be a strong or weak basic water-absorbing resins. The basic water-absorbing resin can be a single resin or a mixture of resins. The basic resin can be a homopolymer or a copolymer. The identity of the basic resin is not limited as long as the basic resin is capable of reacting with a surface-crosslinking agent. The strong basic resins typically are present in the hydroxide (OH) or bicarbonate (HCO$_3$) form.

The basic water-absorbing resin typically is a lightly crosslinked resin, such as a poly(vinylamine). The basic resin also can be a lightly crosslinked polyethylenimine, a poly (allylamine), a poly(allylguanidine), a poly(dimethyldiallylammonium hydroxide), a quaternized polystyrene derivative, such as

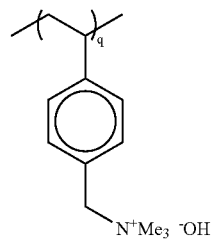

a guanidine-modified polystyrene, such as

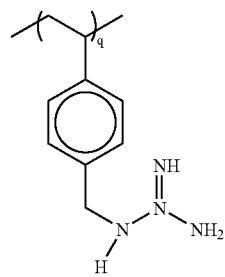

a quaternized poly((meth)acrylamide) or ester analog, such as

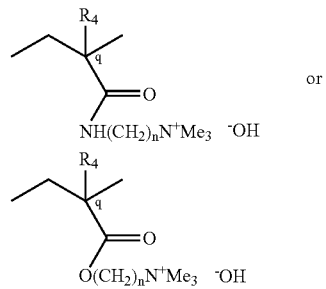

wherein Me is methyl, $R_4$ is hydrogen or methyl, n is a number 1 to 8, and q is a number from 10 to about 100,000, or a poly(vinylguanidine), i.e., poly(VG), a strong basic water-absorbing resin having the general structural formula

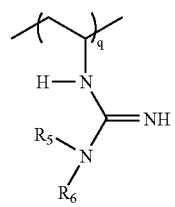

wherein q is a number from 10 to about 100,000, and $R_5$ and $R_6$, independently, are selected from the group consisting of hydrogen, $C_{1-4}$ alkyl, $C_{3-6}$ cycloalkyl, benzyl, phenyl, alkyl-substituted phenyl, naphthyl, and similar aliphatic and aromatic groups. The lightly crosslinked basic water-absorbing resin can contain other copolymerizable units and is crosslinked using a polyfunctional organic compound, as set forth above with respect to the acidic water-absorbing resin.

A basic water-absorbing resin used in the present SAP particles typically contains an amino or a guanidine group. Accordingly, a water-soluble basic resin can be crosslinked internally in solution by suspending or dissolving an uncrosslinked basic resin in an aqueous or alcoholic medium, then adding a di- or polyfunctional compound capable of internally crosslinking the basic resin by reaction with the amino groups of the basic resin. Such crosslinking agents include, for example, multifunctional aldehydes (e.g., glutaraldehyde), multifunctional acrylates (e.g., butanediol diacrylate, TMPTA), halohydrins (e.g., epichlorohydrin), dihalides (e.g., dibromopropane), disulfonate esters (e.g., $ZS(O_2)$ O—$(CH_2)$n-$OF(O)_2Z$, wherein n is 1 to 10, and Z is methyl or tosyl), multifunctional epoxies (e.g., ethylene glycol diglycidyl ether), multifunctional esters (e.g., dimethyl adipate), multifunctional acid halides (e.g., oxalyl chloride), multifunctional carboxylic acids (e.g., succinic acid), carboxylic acid anhydrides (e.g., succinic anhydride), organic titanates (e.g., TYZOR AA from DuPont), melamine resins (e.g., CYMEL 301, CYMEL 303, CYMEL 370, and CYMEL 373 from Cytec Industries, Wayne, N.J.), hydroxymethyl ureas (e.g., N,N'-dihydroxymethyl-4,5-dihydroxyethyleneurea), and multifunctional isocyanates (e.g., toluene diisocyanate or methylene diisocyanate). Internal crosslinking agents for basic resins also are disclosed in Pinschmidt, Jr. et al. U.S. Pat. No. 5,085,787, incorporated herein by reference, and in EP 450 923.

Conventionally, the internal crosslinking agent is water or alcohol soluble, and possesses sufficient reactivity with the basic resin such that crosslinking occurs in a controlled fashion, preferably at a temperature of about 25° C. to about 150° C. Preferred internal crosslinking agents are ethylene glycol diglycidyl ether (EGDGE), a water-soluble diglycidyl ether, and a dibromoalkane.

The basic resin, either strongly or weakly basic, therefore, can be any resin that acts as an SAP in its charged form. Examples of basic resins include a poly(vinylamine), a polyethylenimine, a poly(vinylguanidine), a poly(allylamine), a poly(allylguanidine), or a poly(dialkylaminoalkyl (meth) acrylamide) prepared by polymerizing and lightly crosslinking a monomer having the structure

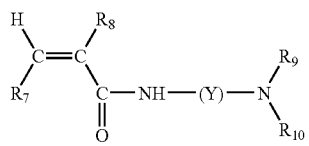

or its ester analog

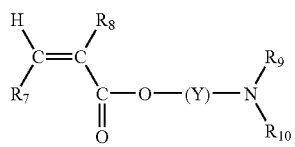

wherein $R_7$ and $R_8$, independently, are selected from the group consisting of hydrogen and methyl, Y is a divalent straight chain or branched organic radical having 1 to 8 carbon atoms, $R_9$ is hydrogen, and $R_{10}$ is hydrogen or an alkyl radical having 1 to 4 carbon atoms. Preferred basic resins include a poly(vinylamine), polyethylenimine, poly(vinylguanadine), poly(methylaminoethyl acrylamide), and poly(methylaminopropyl methacrylamide).

There is no restriction on the shape of the SAP particles used in the present surface-crosslinking method. The SAP particles can be in the form of spheres obtained by inverse phase suspension polymerization, flakes obtained by drum drying, or irregularly shaped particles obtained by pulverizing solid polymer. From the standpoint of the speed of absorption, the SAP particles preferably are small, and typically the particle size is about 20 to about 2000 μm, preferably about 50 about 850 μm.

Surface crosslinking of SAP particles is achieved by spraying SAP particles with a solution containing a surface-crosslinking agent to wet predominantly only the outer surfaces of the SAP particle. Drying of the surface-treated SAP particles then is performed, preferably by heating at least the wetted surfaces of the SAP particles. Surface treatment and heating results in surface crosslinking of the SAP particles.

Typically, the SAP particles are surface treated with an aqueous solution centering a surface-crosslinking agent. The solution contains about 0.01 to about 5%, and preferably about 0.4% to about 3%, by weight, of a surface-crosslinking agent. The solution can be applied as a fine spray onto the surface of freely tumbling SAP particles at a ratio of about 1:0.01 to about 1:0.5 parts by weight SAP particles to solution of surface-crosslinking agent. The surface-crosslinking agent is present in an amount of 0% to about 1%, and preferably 0 to about 0.5% by weight, of the SAP particles. To achieve the full advantage of the present invention, the surface-crosslinking agent is present in an amount of about 0.001% to about 0.3% by weight of the SAP particles.

The crosslinking reaction and drying of the surface-treated SAP particles are achieved by heating the surface-treated SAP particles at a suitable temperature, e.g., about 25° C. to about 150° C., and preferably about 105° C. to about 135° C. However, any other method of reacting the surface-crosslinking agent to achieve surface crosslinking of the SAP particles, and any other method of drying the SAP particles, such as microwave energy, or the like, can be used. In accordance with the present invention, heating of the surface-treated SAP particles is performed at a sufficiently low temperature such that the PDO is essentially excluded from surface crosslinking reactions.

With respect to SAP particles comprising an acidic resin, suitable surface-crosslinking agents are capable of reacting with acid moieties and crosslinking the acidic resin. The surface-crosslinking agent is water soluble or dispersible, and possesses sufficient reactivity with an acidic resin such that crosslinking occurs at a temperature of about 25° C. to about 150° C.

Nonlimiting examples of suitable surface-crosslinking agents for SAP particles comprising an acidic resin include:
(a) metal salts;
(b) quaternary ammonium compounds;
(c) a multifunctional epoxy compound;
(d) an alkylene carbonate, like ethylene carbonate or propylene carbonate;
(e) a polyaziridine, like 2,2-bishydroxymethyl butanol tris [3-(1-aziridine propionate]);
(f) a haloepoxy, like epichlorhydrin;
(g) a polyamine, like ethylenediamine; and
(h) other crosslinking agents for acidic resins known to persons skilled in the art.

Other useful surface-crosslinking agents are the hydroxyalkylamides disclosed in U.S. Pat. No. 6,239,230; 2-oxazolidone and derivatives thereof disclosed in WO 99/42494; 2-oxotetrahydro-1,3-oxazine and derivatives disclosed in WO 00/31153; N-aryl-2-oxazolidones disclosed in WO 00/31152; and poly-2-oxazolidinones in WO 99/43720, each incorporated herein by reference.

With respect to SAP particles comprising a basic resin, suitable surface-crosslinking agents include di- or polyfunctional molecules capable of reacting with amino groups and crosslinking a basic resin. The surface-crosslinking agent is water soluble or dispersible and possesses sufficient reactivity with a basic resin such that surface cross-linking occurs at a temperature of about 25° C. to about 150° C.

Nonlimiting examples of suitable surface-crosslinking agents for SAP particles comprising a basic resins include:

(a) dihalides and disulfonate esters, for example, compounds of the formula

wherein p is a number from 2 to 12, and Y, independently, is halo (preferably bromo), tosylate, mesylate, or other alkyl or aryl sulfonate esters;

(b) multifunctional aziridines;

(c) multifunctional aldehydes, for example, glutaraldehyde, trioxane, paragormaldehyde, terephthaldehyde, malonaldehyde, and glyoxal, and acetals and bisulfites thereof;

(d) halohydrins, like epichlorohydrin;

(e) multifunctional epoxy compounds, for example, ethylene glycol diglycidyl ether, bisphenol A diglycidyl ether, and bisphenol F diglycidyl ether, (f) multifunctional carboxylic acids, and esters and anhydrides derived therefrom, for example, di- and polycarboxylic acids containing 2 to 12 carbon atoms, and the methyl and ethyl esters, and anhydrides derived therefrom, like oxalic acid, succinic acid, malonic acid, and glutaric acid, and esters and anhydrides derived therefrom;

(g) organic titanates, like TYZOR AA, available from E.I. DuPont de Nemours, Wilmington, Del.;

(h) melamine resins, like the CYMEL resins available from Cytec Industries, Wayne, N.J.;

(i) hydroxymethyl ureas, like N,N'-dihydroxymethyl-4,5-dihydroxyethylene urea; and (j) other crosslinking agents for basic water-absorbing resins known to persons skilled in the art.

A preferred surface-crosslinking agent is ethylene glycol diglycidyl ether (EGDGE) which crosslinks a basic resin at a temperature of about 25° C. to about 150° C.

A surface-crosslinker solution utilized in the present method comprises water, a sufficient amount of a surface-crosslinking agent to provide a predetermined degree of surface crosslinking, and about 20 to about 35 wt % of PDO. Preferably, the surface crosslinker solution contains about 25 to about 30 wt % of PDO. The components of the surface crosslinker solution are simply admixed to provide a homogeneous solution.

In preferred embodiments, the surface-crosslinker solution consists essentially of a surface-crosslinking agent, water, and PDO. In most preferred embodiments, the surface-crosslinker solution is free of PG.

Surprisingly, it was found that the amount of surface-crosslinking agent in the composition required to achieve a predetermined degree of surface crosslinking could be reduced when PDO is used as a cosolvent, compared to a surface crosslinking solution that utilizes PG as the cosolvent. In particular, it was found that the amount of surface-crosslinking agent in a surface-crosslinker solution utilizing PDO can be reduced by at least 5 wt %, and typically about 10 wt % to about 25 wt %, to achieve the same degree of surface crosslinking provided by a solution containing PG.

After applying a sufficient amount of a surface-crosslinker solution to the surfaces of SAP particles, drying and surface crosslinking of the surface-treated SAP particles are achieved by heating the surface-treated particles at a suitable temperature, e.g., about 25° C. to about 150° C., and preferably about 105° C. to about 150° C. To achieve the full advantage of the present invention, the surface-treated particles are heated at about 110° C. to about 140° C. At this temperature, the SAP particles are surface crosslinked by the surface-crosslinking agent without degrading the color of the SAP particles and without increasing the residual monomer content of the SAP particles.

The surface-treated SAP particles are heated for about 15 to about 180 minutes, preferably about 15 to about 150 minutes, to effect surface crosslinking. To achieve the full advantage of the present invention, the surface-treated SAP particles are heated for about 30 to about 120 minutes.

At these surface-crosslinking temperatures and times, the PDO does not undergo the surface crosslinking reaction to any reasonable extent, i.e., less than about 3% and typically less than 1%, of the PDO present in the surface-crosslinking composition is involved in surface-crosslinking.

Ordinary dryers or heating ovens can be used for heating the surface-treated SAP particles. Such heating apparatus includes, for example, a tray dryer, an agitated trough dryer, a rotating dryer, a rotating disc dryer, a kneading dryer, a fluidized bed dryer, a pneumatic conveying dryer, and an infrared dryer. However, any other method of reacting the surface-crosslinking agent with the polymer of the SAP particle to achieve surface crosslinking, such as microwave energy, can be used. In the surface treating and surface crosslinking steps, the mixer can be used to perform simultaneous mixing and heating of the surface-crosslinking agent and SAP particles, if the mixer is of a type that can be heated.

For both contact dryers (like tray dryers) and noncontact dryers (like disk dryers), the greater oxidative stability and lower volatility of PDO provides a cleaner manufacturing process. When using PG, oxidative build-up results in lost production time, increased waste, and higher equipment maintenance costs. For example, expensive filters used to clean air after the surface-crosslinking process need to be changed more frequently when PG is used compared to PDO. The advantages of the present invention are most dramatic when a high airflow dryer is used, such as a tray dryer. Brown to black PG oxidation products form on the interior walls of such dryers which result in fouling and product contamination. This problem is substantially reduced with the use of PDO as a cosolvent. Also, the higher temperature required with surface-crosslinking agents such as propylene carbonate would benefit from the use of PDO because of its high stability and low vapor pressure.

As previously stated, surface treating with a surface-crosslinking agent, and subsequent or simultaneous heating, provides additional polymer crosslinks in the vicinity of the surface of the SAP particles. The gradation in crosslinking from the surface of the SAP particles to interior, i.e., the anisotropy of crosslink density, can vary, both in depth and profile. Thus, for example, the depth of surface crosslinking can be shallow, with a relatively sharp transition from a high level to a low level of crosslinking. Alternatively, for example, the depth of surface crosslinking can be a significant fraction of the dimensions of the SAP particle, with a broader transition.

Depending on size, shape, porosity, as well as functional considerations, the degree and gradient of surface crosslinking can vary within a given type of SAP particle. Depending on variations in surface:volume ratio within the SAP particles (e.g., between small and large particles), it is typical for the overall level of crosslinking to vary over the group of SAP particles (e.g., is greater for smaller particles).

Surface crosslinking generally is performed after the final boundaries of the SAP particles are essentially established (e.g., by grinding, extruding, or foaming). However, it is also possible to effect surface crosslinking concurrently with the creation of final boundaries. Furthermore, some additional changes in SAP particle boundaries can occur even after surface crosslinks are introduced.

The following examples illustrate the present method of surface crosslinking SAP particles. It should be understood, however, that these examples are merely illustrative, and that the scope of the present invention is not limited to these examples. In these examples, the SAP particles were commercially prepared, lightly crosslinked polyacrylic acid polymers, neutralized about 75% to about 80% with sodium hydroxide.

The surface-crosslinked SAP particles were tested for absorption under load at 0.7 psi (AUL (0.7 psi)). Absorption under load (AUL) is a measure of the ability of an SAP to absorb fluid under an applied pressure. The AUL was determined by the following method as disclosed in U.S. Pat. No. 5,149,335, incorporated herein by reference.

An SAP (0.160 g±0.001 g) is carefully scattered onto a 140-micron, water-permeable mesh attached to the base of a hollow Plexiglas cylinder with an internal diameter of 25 mm. The sample is covered with a 250 g cover plate and the cylinder assembly weighed. This gives an applied pressure of 51 g/cm$^2$ (0.7 psi). The screened base of the cylinder is placed in a 100 mm Petri dish containing 25 milliliters of a test solution (usually 0.9% saline), and the polymer is allowed to absorb for 1 hour (or 3 hours). By reweighing the cylinder assembly, the AUL (at a given pressure) is calculated by dividing the weight of liquid absorbed by the dry weight of polymer before liquid contact.

The test results in Table 2 also set forth the centrifuge retention capacity (CRC) of the test samples. The centrifuge retention capacity of an SAP is a measure of the absorptive capacity of the SAP. In particular, the CRC test is a method of determining the absorbent capacity of an SAP in grams of 0.9% saline (NaCl) solution per gram of polymer. This test includes swelling the SAP in a "teabag" immersed in 0.9% NaCl solution for 30 minutes, then centrifuged for three minutes. The ratio of retained liquid weight to initial weight of the dry SAP is the absorptive capacity of the superabsorbent polymer, or the CRC.

The CRC test measures the free swellability of an SAP hydrogel in a teabag. The CRC test was performed as follows:

Dry SAP particles (0.2000±0.0050 g, particle size fraction 106-850 μm) are weighed into a teabag 60×85 mm in size which then is sealed. The teabag is placed in an excess of 0.9% by weight sodium chloride solution (at least 0.83 l of sodium chloride solution/1 g of polymer powder) for 30 minutes. The teabag then is centrifuged for 3 minutes at 250 g. The amount of liquid is determined by weighing the centrifuged teabag. Measurement of CRC also is disclosed in Woodrum et al. U.S. Pat. No. 6,187,828 and Gartner et al. U.S. Pat. No. 5,633,316, each incorporated herein by reference.

EXAMPLE 1

A Cuisinart Mini-Prep Processor was charged with 50 g of SAP particles having a centrifuge retention capacity (CRC) of 40.8 g/g. With the processor running on high speed, a solution (1.8 g) containing 19% propylene glycol, 80% water, and 1% ethylene glycol diglycidyl ether, by weight, was introduced via syringe (22 gauge needle) over 30 seconds. The surface-treated SAP particles then were distributed on a drying tray to a depth of 0.25 inch and dried in a high transverse airflow oven. The drying temperature started at 55° C. for 5 minutes, then ramped up to 135° C. over 73 minutes.

The same procedure was followed using a surface-crosslinker solution containing 19 wt % 1,3-propanediol as a substitute for the propylene glycol. The results are summarized in the following Table 1.

TABLE 1

| Cosolvent | AUL #1 | AUL #2 | AUL #3 | Ave. | StDev |
|---|---|---|---|---|---|
| 1,2-propanediol | 18.41 | 17.97 | 17.97 | 18.12 | 0.25 |
| propylene glycol | 16.72 | 13.96 | 15.37 | 15.35 | 1.35 |

As seen in Table 1, using 1,3-propanediol as a cosolvent imparts improved AUL (0.7 psi) (absorbence under load at 0.7 psi) values (i.e., 18.12 g/g vs. 15.35 g/g) to the SAP particles. In addition, variability of SAP particles in production is reduced, i.e., AUL variability is reduced when PDO is the cosolvent (i.e., standard deviation is 1.38 g/g using PG compared to 0.25 g/g using PDO). Accordingly, production of SAPs using 1,3-propanediol as a cosolvent provides SAP particles having more uniform and consistent properties.

EXAMPLE 2

The procedure of Example 1 was repeated except the ratio of water to cosolvent was varied. The results summarized below show that the optimum level of cosolvent needed to achieve optimum coating efficiency is lower using 1,3-propanediol as a cosolvent (i.e., about 30 wt %) compared to propylene glycol (i.e., about 37 wt %).

|  | CRC | AUL (0.7) |
|---|---|---|
| 1,3-Propanediol (%) |  |  |
| 19 | 29.5 | 21.2 |
| 25 | 29.9 | 22.6 |
| 35 | 31.3 | 23.9 |
| 50 | 31.6 | 13.1 |
| Propylene Glycol (%) |  |  |
| 17.7 | 30.36 | 21.62 |
| 21.9 | 29.40 | 21.44 |
| 27.1 | 28.11 | 21.78 |
| 37.5 | 29.41 | 21.86 |
| 58.3 | 30.47 | 20.47 |
| 49.2 | 34.75 | 14.08 |

FIG. 1 shows the positive affect of PDO on AUL (0.7), wherein AUL (0.7) values increase between 20 and 35 wt %. In contrast, PG does not have any positive effects on AUL (0.7) values.

EXAMPLE 3

The procedure of Example 1 was repeated using varying amounts of ethylene glycol diglycidyl ether as the surface-crosslinking agent. The results are summarized in the following Table 2.

TABLE 2

| Cosolvent | EGDGE (ppm) | AUL (0.7) (g/g) | CRC |
|---|---|---|---|
| 1,3-Propanediol | 100 | 10.08 | 35.46 |
| | 200 | 14.92 | 33.62 |
| | 300 | 17.32 | 32.35 |
| | 400 | 20.78 | 31.19 |
| | 800 | 22.28 | 28.33 |
| | 1200 | 22.22 | 28.21 |
| Propylene glycol | 100 | 10.25 | 36.80 |
| | 200 | 12.07 | 34.65 |
| | 300 | 16.13 | 32.97 |
| | 400 | 20.73 | 31.74 |
| | 800 | 21.16 | 29.47 |
| | 1200 | 20.75 | 28.05 |

Table 2 shows that superior AUL values were achieved using 1,3-propanediol as a cosolvent compared to a propylene glycol cosolvent. Therefore, in combination with PDO, less EGDGE can be used to achieve the same AUL development compared to PG.

The above results show that utilizing PDO as a cosolvent in a surface-crosslinking step improves the SAP manufacturing process and improves SAP performance. In particular, the use of PDO improves process efficiency, reduces the amount of surface crosslinking agent that is needed to effectively surface crosslink SAP particles and improve AUL.

In addition, using PDO as a cosolvent renders the surface-crosslinking step more efficient. This allows the amount of surface-crosslinking agent to be decreased by up to 25%, by weight, to achieve the same level of surface crosslinking agent compared to using PG and a greater amount of surface-crosslinking agent.

The surface-crosslinked SAP particles of the present invention can be used as an absorbent in disposable diapers, sanitary napkins, and similar articles, and can be used in other applications, for example, a dew-formation inhibitor for building materials, a water-holding agent for agriculture and horticulture, and a drying agent.

Many modifications and variations of the invention as hereinbefore set forth can be made without departing from the spirit and scope thereof and, therefore, only such limitations should be imposed as are indicated by the appended claims.

What is claimed is:

1. A method of surface cross-linking a superabsorbent polymer comprising the steps of:
   (a) providing superabsorbent polymer particles;
   (b) forming a surface-crosslinker composition comprising ethylene glycol diglycidyl ether, water, and 20 to 35 wt % of 1,3-propanediol as a cosolvent;
   (c) applying the solution of (b) to the surfaces of (a) to provide surface-treated superabsorbent polymer particles; and
   (d) heating the surface-treated superabsorbent polymer particles at 25° C. to 150° C. for 15 to 180 minutes to form surface crosslinks in the vicinity of the surface of the surface-treated superabsorbent polymer particles,
   wherein the amount of ethylene glycol diglycidyl ether in (b) is at least 5 wt % less than the ethylene glycol diglycidyl ether used when propylene glycol is a cosolvent to achieve a predetermined degree of surface crosslinking.

2. The method of claim 1 wherein step (c) is performed prior to step (d).

3. The method of claim 1 wherein steps (c) and (d) are performed simultaneously.

4. The method of claim 1 wherein the amount of ethylene glycol diglycidyl ether in (b) is at least 10 wt % less than the ethylene glycol diglycidyl ether used when propylene glycol is used as a cosolvent to achieve a predetermined degree of surface crosslinking.

5. The method of claim 1 wherein the amount of ethylene glycol diglycidyl ether in (b) is 5 wt % to 25 wt % less than the ethylene glycol diglycidyl ether used when propylene glycol is used as a cosolvent to achieve a predetermined degree of surface crosslinking.

6. The method of claim 1 wherein the surface-crosslinking solution comprises 25 to 30 wt % of the 1,3-propanediol.

7. The method of claim 1 wherein the surface-crosslinking solution is free of propylene glycol.

8. The method of claim 1 wherein the surface-crosslinker solution consists essentially of ethylene glycol diglycidyl ether, water, and 1,3-propanediol.

9. The method of claim 1 wherein the surface crosslinks are formed by essentially only the ethylene glycol diglycidyl ether.

10. The method of claim 1 wherein the superabsorbent polymer comprises a neutralized lightly crosslinked acrylic-type resin containing at least 10% acidic monomer units selected from the group consisting of a carboxylate, sulfonate, sulfate, and phosphate group.

11. The method of claim 1 wherein the superabsorbent polymer comprises polyacrylic acid neutralized 50 to 100 mole percent.

12. A surface-crosslinked superabsorbent polymer prepared by the method of claim 1.

* * * * *